(12) United States Patent
Schimmoller et al.

(10) Patent No.: US 7,096,749 B2
(45) Date of Patent: Aug. 29, 2006

(54) AIR SAMPLING DEVICE AND METHOD

(75) Inventors: Brian J. Schimmoller, Austin, TX (US); Matthew F. Bartlett, Austin, TX (US)

(73) Assignee: Signature Science LLC, Austin, TX (US)

( * ) Notice: Subject to any disclaimer, the term of this patent is extended or adjusted under 35 U.S.C. 154(b) by 195 days.

(21) Appl. No.: 10/601,302

(22) Filed: Jun. 6, 2003

(65) Prior Publication Data

US 2004/0050183 A1    Mar. 18, 2004

Related U.S. Application Data

(60) Provisional application No. 60/387,228, filed on Jun. 7, 2002.

(51) Int. Cl.
*G01N 1/00* (2006.01)

(52) U.S. Cl. .................. 73/863.21; 73/864.31

(58) Field of Classification Search ............ 73/863.21, 73/86.23, 863.25, 863.51, 863.22, 863.52, 73/864, 864.32, 864.33, 864.51, 864.31; 95/277

See application file for complete search history.

(56) References Cited

U.S. PATENT DOCUMENTS

| 3,710,557 | A | * | 1/1973 | Couchman et al. | ....... 73/863.23 |
| 3,802,167 | A | * | 4/1974 | Turman | ................ 73/864.31 |
| 3,868,222 | A | * | 2/1975 | Barringer | .................. 436/29 |
| 3,977,479 | A | * | 8/1976 | Sainsbury | .................. 175/58 |
| 6,524,670 | B1 | * | 2/2003 | Kataoka | ................... 428/35.2 |
| 6,532,835 | B1 | * | 3/2003 | Saaski et al. | ............ 73/863.21 |

OTHER PUBLICATIONS

The American Heritage Dictionary, p. 90, 1982.*

* cited by examiner

*Primary Examiner*—Robert Raevis
(74) *Attorney, Agent, or Firm*—Jackson Walker, LLP (57) ABSTRACT

A lightweight, economical, mass-producible, reusable airfoil can be deployed in an airspace while in or attached to any moving vehicle for the purpose of collecting air samples. A frame has an airfoil shape that provides pressure differentials that preferentially direct particulates and contaminants of differing size and mass to different areas of an absorbent media attached or integral to the frame. The absorbent media are readily detachable from the frame for sanitary and efficient transfer to facilities where the samples can be analyzed.

11 Claims, 9 Drawing Sheets

AIR SAMPLING DEVICE AND METHOD

This application claims priority from provisional patent No. 60/387,228 filed Jun. 7, 2002.

FIELD OF INVENTION

This invention pertains to the field of air sampling devices, more specifically, an air sampler in the general shape of an airfoil and a method for sampling air using the airfoil shaped sampler.

BACKGROUND

The collection of statistically significant quantities of particulates and contaminants of interest in atmospheric analysis typically requires high rates of airflow. Electromechanical air-moving devices such as pumps, fans, and blowers force air over devices such as filters and absorbents in order to provide the required airflow in typical sampling applications. Such active air-moving devices are generally costly, noisy, and heavy, and require a power source.

A need exists for a small lightweight particulate air sampler designed for use on the earth's surface as well as on vehicles. A need exists for a small lightweight air sampling device for detection of airborne chemicals particulate and contaminants at low levels of concentration. Military, homeland defense and other demands exists for an inexpensive vehicle mounted air sampler.

SUMMARY OF THE INVENTION

Applicants provide an air sampling device comprised of a frame and media members, the media members for engaging the frame, and the device for passing through the air to collect particulates when the air passes through the media members. More specifically, Applicants provide a frame for engaging media members, the frame constructed in the shape of one or more airfoils, having leading and trailing edges.

Figure 1:
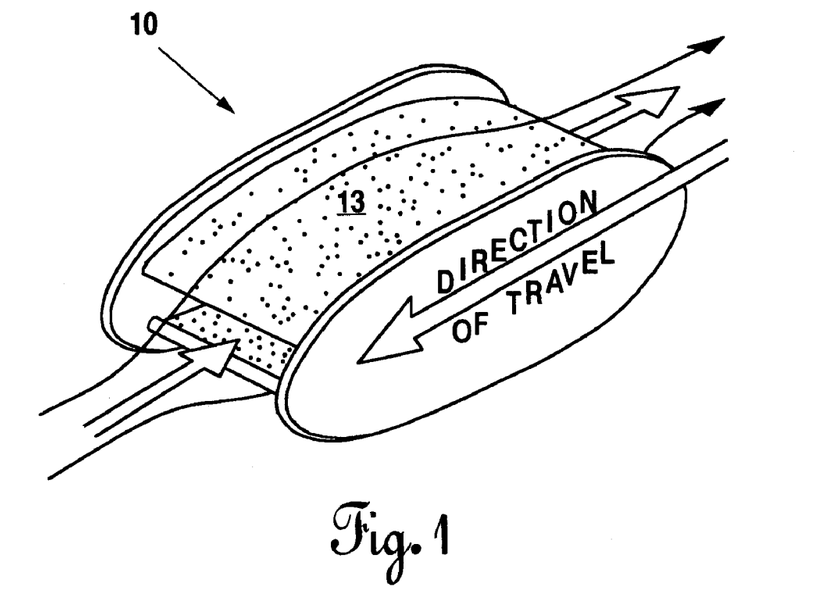
Figure 2:
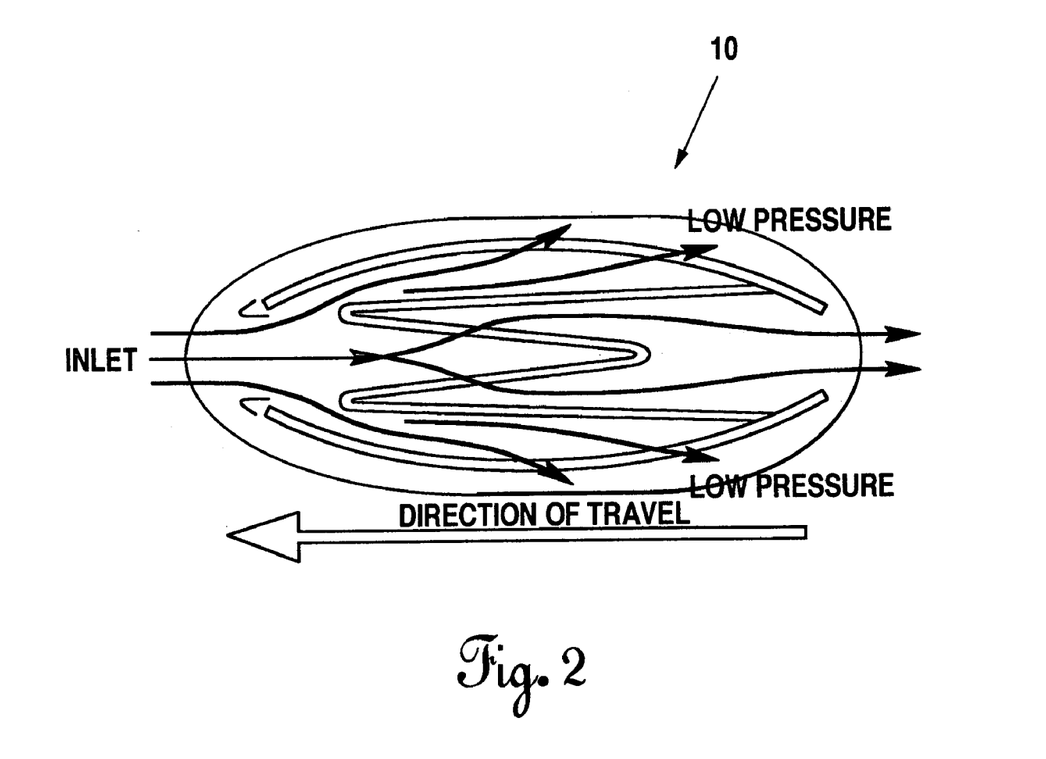
Figure 3:
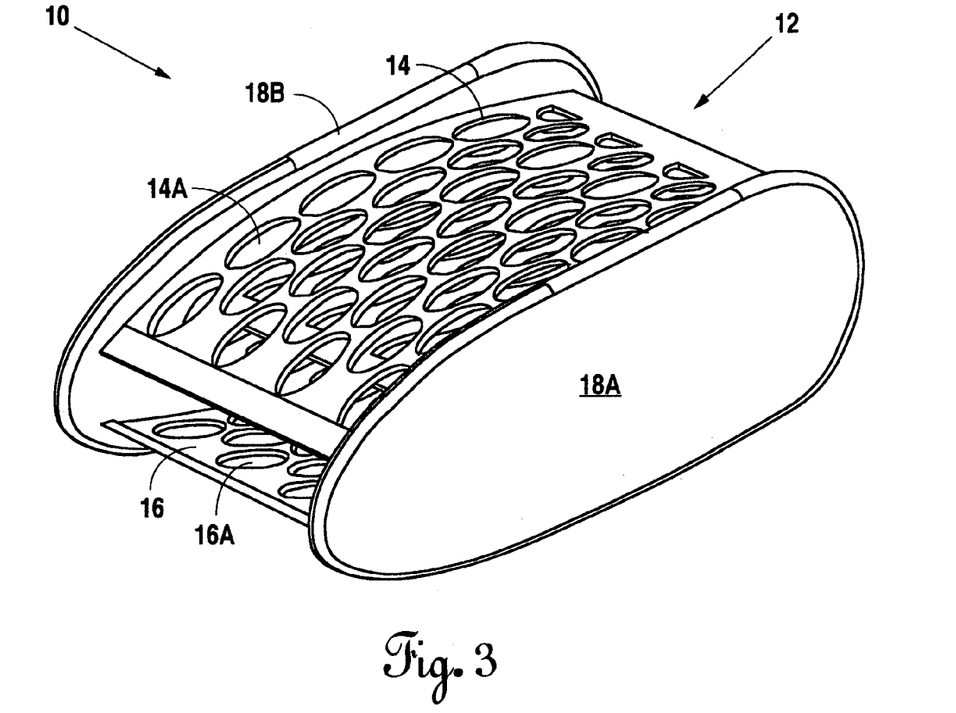
Figure 4:
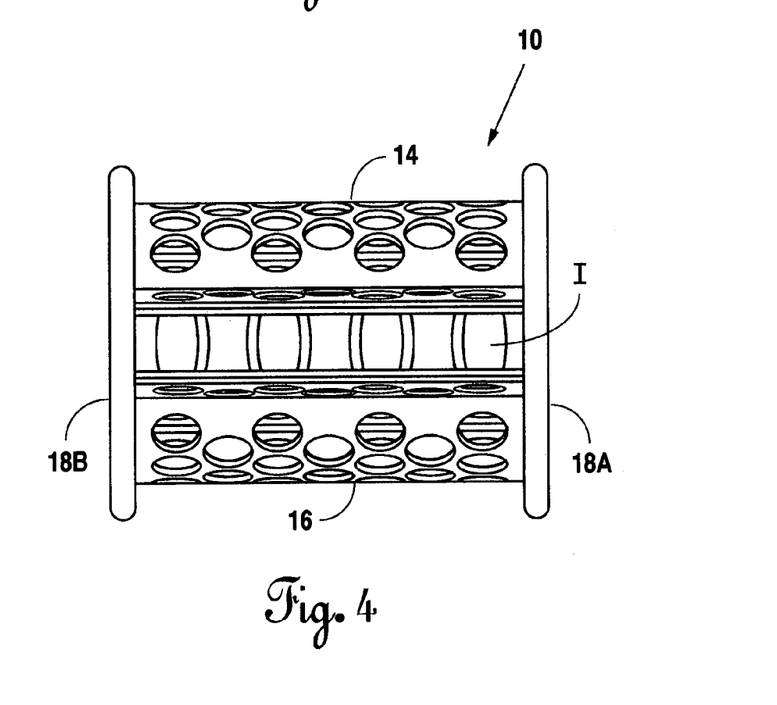
Figure 5:
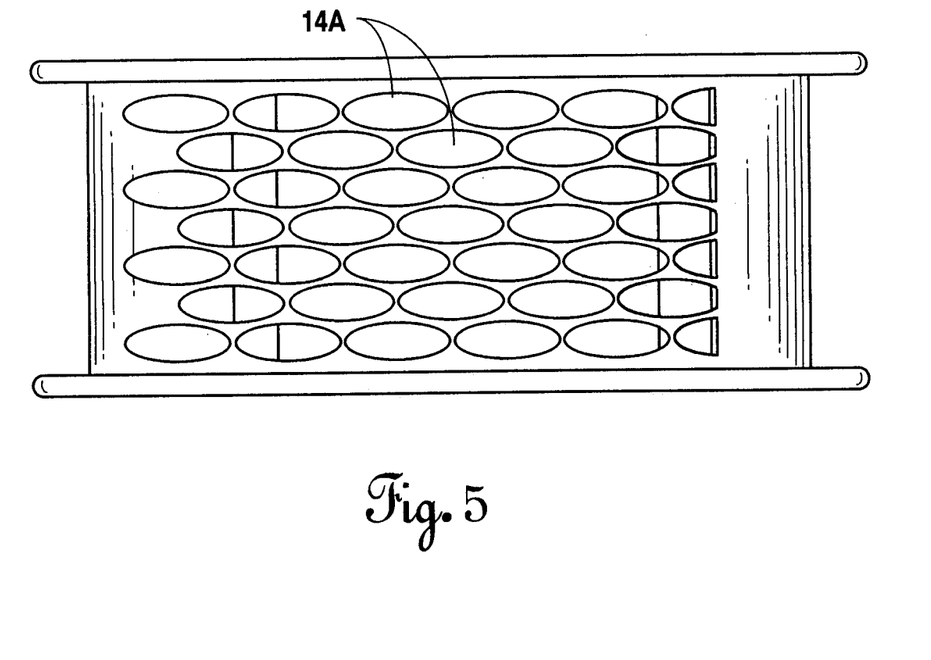
Figure 6:
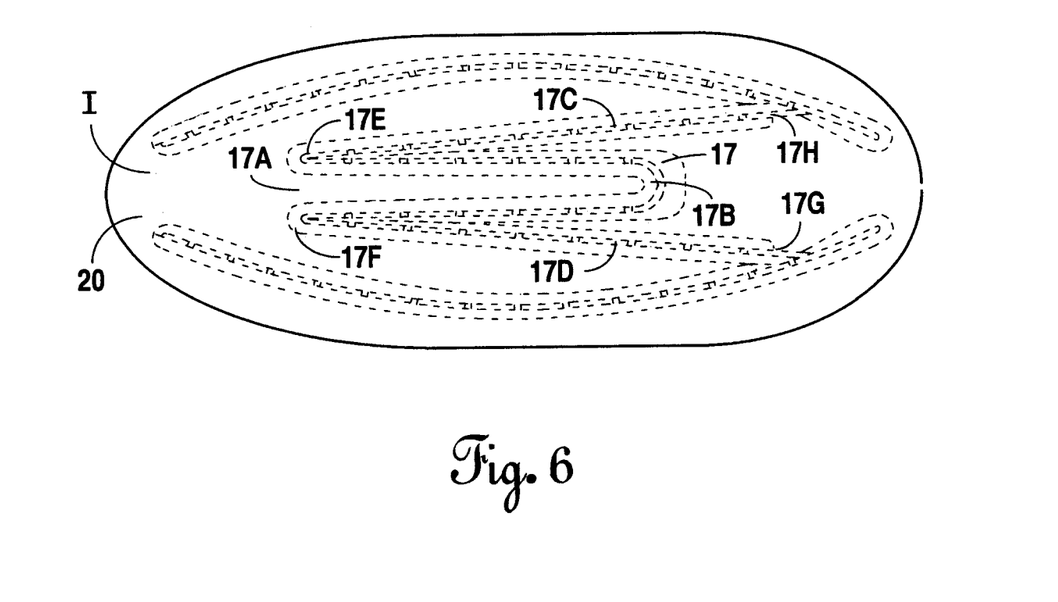
Figure 7:
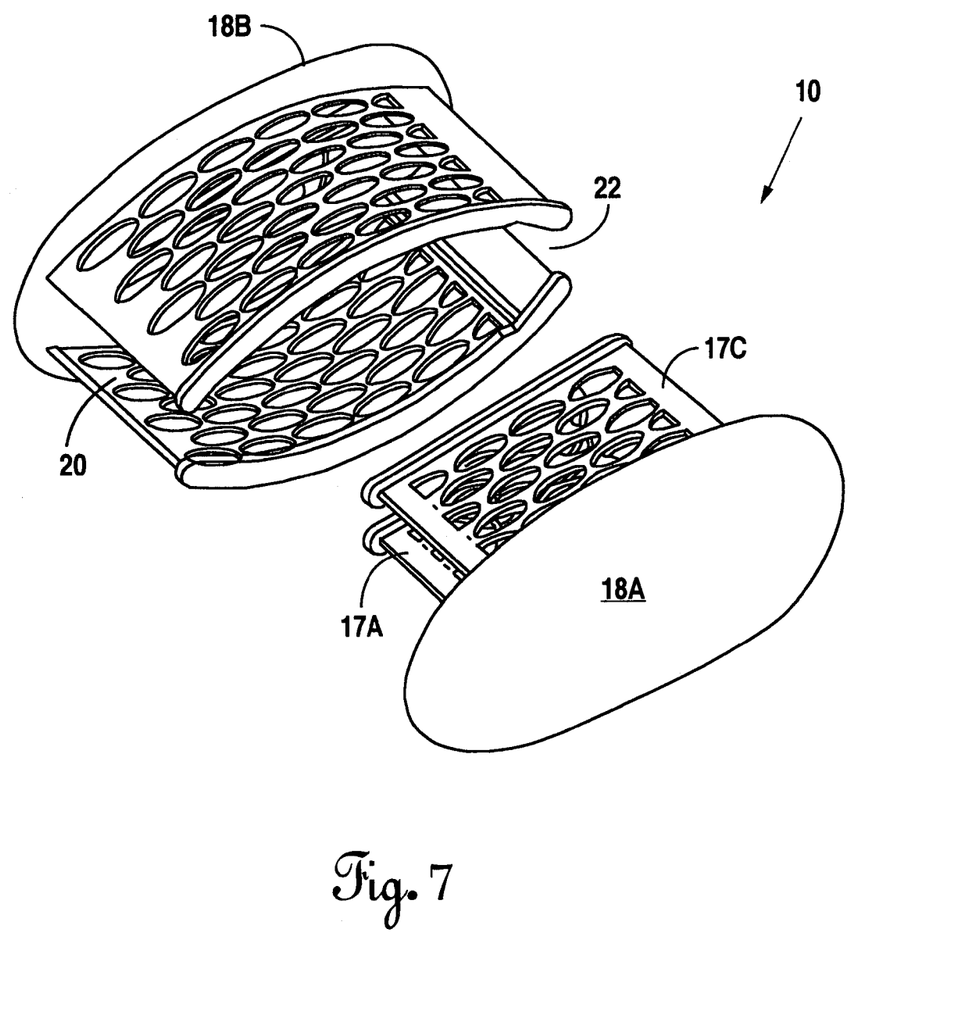

The airfoil shaped apparatus is effective, lightweight, inexpensive, and capable of mass production. It mounts to any moving carrier, and collects air samples as the carrier moves through the air.

The airfoil shaped device produces differential air pressures and air velocities over its surface according to the application of Bernoulli's law. Differential pressure provides for particulate separation according to mass and size of the individual particles, thus offering a built-in passive filtration capability.

Users of Applicants' airfoil shaped air sampler may use any vehicle, including but not limited to, a lightweight, unmanned, radio-controlled airborne vehicle, including a glider, for deploying the air sampler. Such use provides an efficient, lightweight, and highly mobile platform for Applicants' airfoil shaped air sampler.

The present invention includes a frame constructed in the shape of an airfoil. At the leading and trailing edges the airfoil typically has gaps of varying and variable dimension through which air can pass when the frame is suspended in the airflow in or around the moving carrier. The airfoil shape creates differential pressures and velocities on the top and bottom airfoil surfaces and the leading edge and trailing edge, an effect being that particulates of different size and mass tend to be separated into different air streams over, under, and through the airfoil. The airfoil itself can be constructed, at least in part, of an absorbent media which is sized to pick up particulate matter, or the airfoil may include a frame upon which an absorbent media will rest, the absorbent media for retention of particulate particles as the carrier passes through the air.

The earth sampler device of Applicants' present invention may also be designed to sample airborne chemicals. That is, airborne particulates and/or chemicals may be sampled with Applicants' present device. Indeed, Applicants' present invention may include a second airfoil shape through which a pressure differential can drive an air sample across an absorbent carbon based bed, which would pick up some chemicals in the air.

Applicants' present invention may include a means to mount the airfoil device on a moveable vehicle such as a small, lightweight, unmanned, airborne "drone," a ground vehicle or a water craft. The means to mount may include a power server on gears to fold the air sampling device from a position in the air stream to position out of the air stream.

BRIEF DESCRIPTION OF THE DRAWINGS

FIG. 1 illustrates Applicants' novel air sampler in perspective view showing the relative direction of air travel.

FIG. 2 is a side cross-sectional view of the air sampler showing the top and bottom airfoil sections as well as the frame and absorbent material that may be located between the airfoil sections.

FIG. 3 illustrates a side perspective view of Applicants' novel air sampler without the absorbent media thereon.

FIG. 4 is a front elevational view of the air sampler as illustrated in FIG. 3.

FIG. 5 is a top elevational view of the air sampler as illustrated in FIGS. 3 and 4.

FIG. 6 is a cross-sectional side view of the air sampler of Applicants' present invention showing the frame and the absorbent material placed thereon.

FIG. 7 is an exploded view of the air sampler without the absorbent media engaged with the frame thereof.

FIG. 8A is an assembled view of an alternate preferred embodiment of Applicants' novel air sampler, which embodiment includes a second airfoil.

FIG. 8B is a top elevational cutaway cross-sectional view of the embodiment of the air sampler illustrated in FIG. 8A.

FIG. 8C is an exploded view in perspective of the embodiment of Applicants' air sampler illustrated in FIG. 8A.

FIGS. 9A and 9B illustrate top elevational cutaway views of the air sampler illustrated in FIG. 8A mounted to a fuselage of an aircraft and rotatable between in a closed position (FIG. 9A) and a use position (FIG. 9B).

FIG. 10 is a front elevational view of an aircraft with an air sampler rigidly attached.

DETAILED DESCRIPTION OF THE PREFERRED EMBODIMENT

FIGS. 1 through 7 illustrate Applicants' novel air sampler (10). Air sampler (10) may include a frame (12) at least a portion of which engages an absorbent filter media (13). Frame (12) typically is comprised of at least one airfoil member, the figure here showing an embodiment including an upper airfoil member (14) and a lower airfoil member (16). The members typically have a multiplicity of through-holes (14A and 16A), and may be spaced apart so as to define a leading edge gap (20) and a trailing edge gap (22). End plates (18A and 18B) provide support and location for the upper and lower airfoil members. Between the upper and lower airfoil members, which are typically provided as illustrated in the cross-section of FIG. 2, and are bowed away from each other, there may be a pleated or cup shaped frame member (17). The cup shaped frame member may have an open end (17A) facing the leading edge gap (20) and a closed end (17B) opposite the open end, typically comprising a longitudinal axis that lies on the chord between the leading edge and the trailing edge of the upper and lower airfoil members. The pleat or cup shaped frame member (17) typically attaches to one end plate and may notch into the other (see FIG. 8C) end plate. The pleat or cup shaped member may attach to the inner sides (17G and 17H) of the airfoils. The frame may be made of Duraform® or of any other suitable material and made by SLS (Selected Layer Scintering) or by any suitable method. The frame, including the upper and lower airfoil, the end plates, and the pleated cup shaped frame members may be injection molded from a plastic or other suitable material. Absorbent filter media (13) may be any suitable absorbent media such as Electret™ filters from 3M.

The air sampling device is typically small, in chord about 3.5 inches from leading edge to trailing edge and 1.3 inches in thickness (as measured between the upper and lower airfoils at the maximum point of separation). Chord range is 1.0 to 12.0 inches (preferred) and thickness range is 0.5 to 6.0 inches (preferred). The maximum width as measured across end plates (18A and 18B) is preferably about 1.5 inches (preferred range 0.5 to 3.0 inches) and the leading edges of the cup shaped frame member (17E and 17F) may be spaced apart from the adjacent airfoil by, preferably 0.25 inches (preferred range 0.1 to 1.0 inches). The preferred width of open end (17A) is about 0.5 inches (preferred range 0.1 to 1.0 inches). This is equal, in this embodiment, to the width of the leading edge gap and the trailing edge gap. The length of the inlet (I) defined by the leading edge gap is typically about 1.5 inches. Note that size of inlet (I) is typically about the same as outlet (O) defined by trailing edge gap (22).

Air flows through airfoil surface filters and inside and through the pleated or cup shaped frame member. The cup shaped frame member increases the surface area of the absorbent media that is exposed to the flowing air and tends to collect the particles of highest mass in the center pleat. Thus, the airfoil filter tends to preferentially collect particles separated by mass.

Applicants' novel air sampler (10) works without a pump or a fan. Air is pushed through the filter media by the force of air entering the inlet, and air is pulled through the filter media by the pressure differential that forms across the top and bottom of the upper and lower airfoil members as the airfoil moves through the air. The use of an electrostatic filter media provides a more efficient collection of particulates. Further, the general aerodynamic shape provides a reduction of drag. The lower pressure zones on the airfoil surfaces enhance flow through the filter. The airflow will also separate particulate deposition on absorbent media according to the size and mass of the particles. Computer testing of a model built according to dimensions set forth above yielded, at a speed of approximately 30 mph, 400 liters per minute sample volume.

Figure 8A:
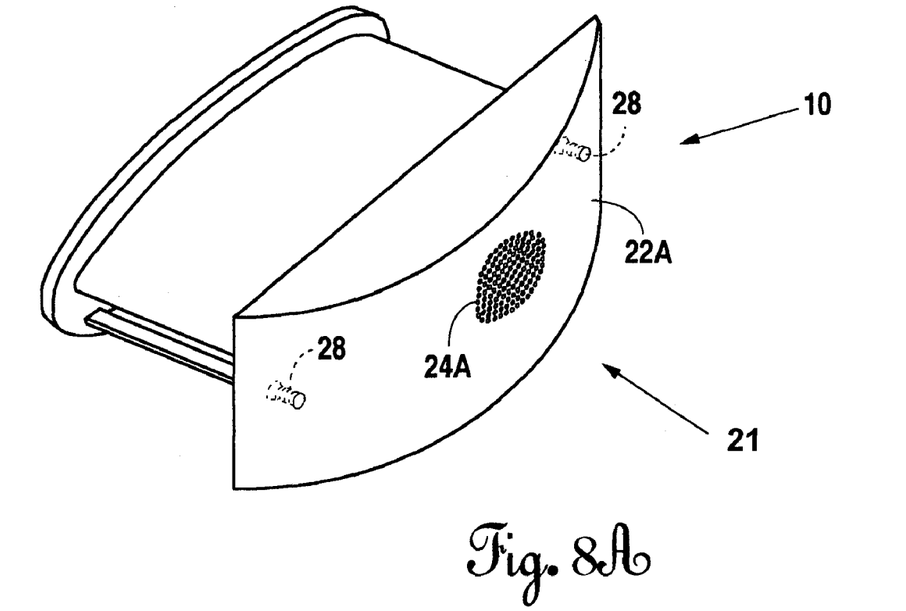
Figure 8B:
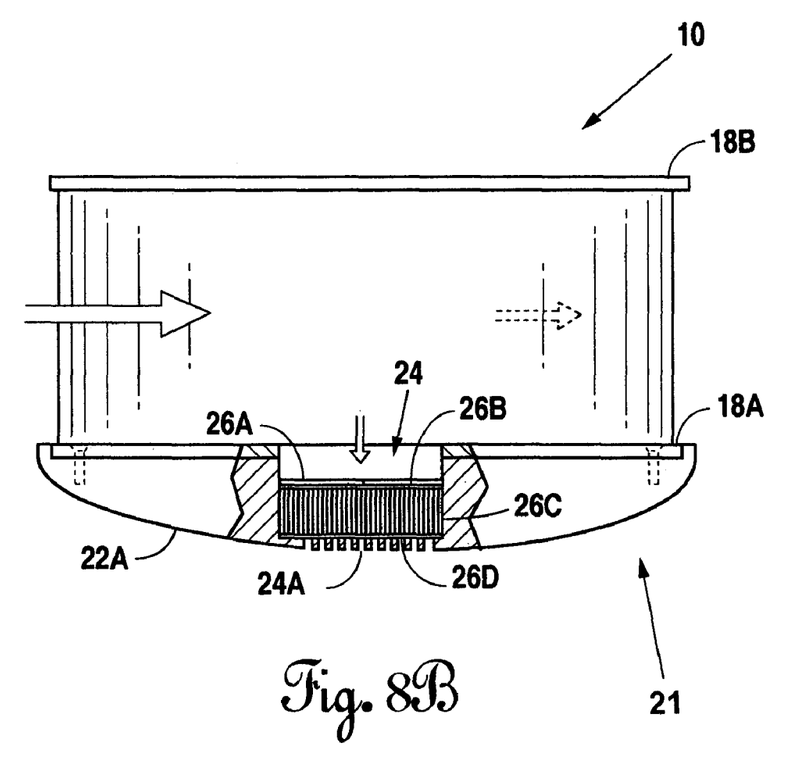
Figure 8C:
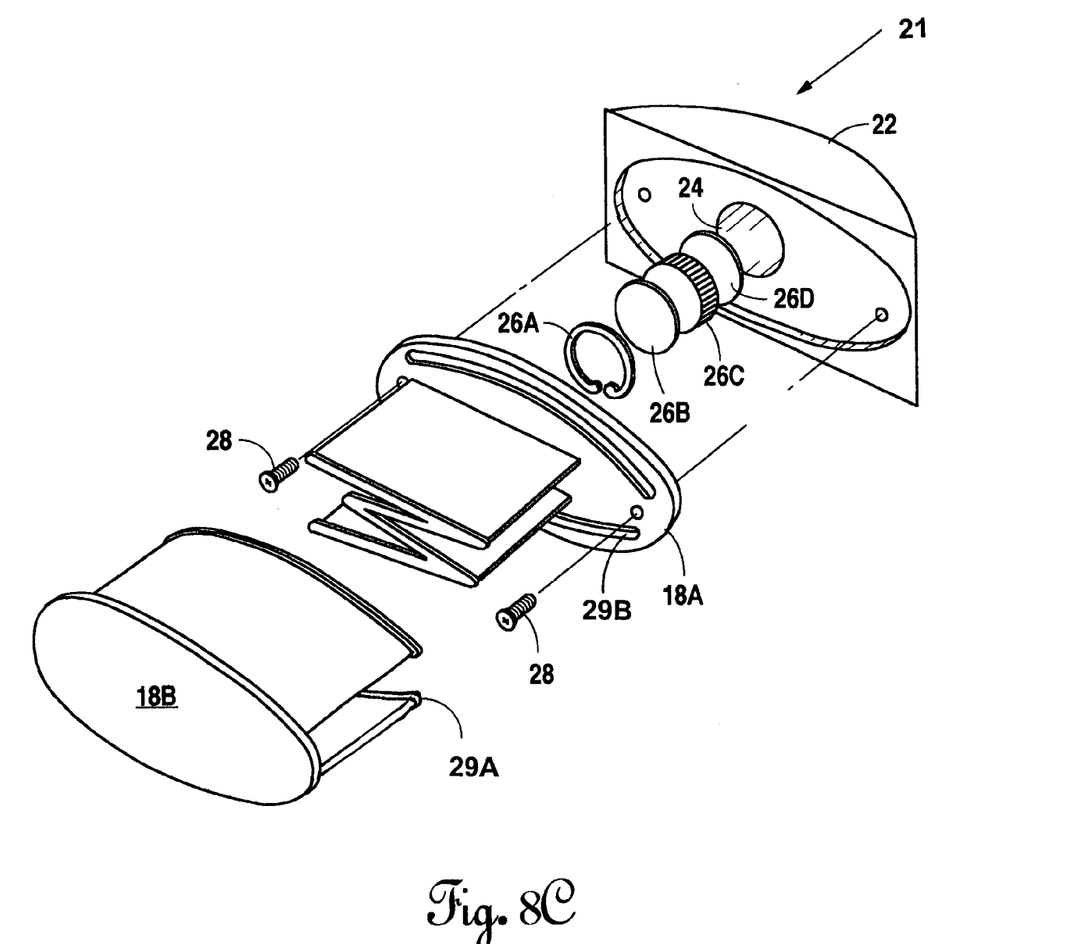

FIGS. 8A, 8B and 8C illustrate a preferred alternate embodiment of Applicants' air sampler (10). In this embodiment, it is seen that a second airfoil (21) is provided, which second airfoil includes a frame or housing (22) having a curved airfoil surface (22A) thereof. This second airfoil may be used to provide sampling for airborne chemical custom contaminates whereas the first airfoil defined by frame 12 may use an absorbent filter designed to physically trap airborne particles. A port (24) is provided in the housing which port will open up to the curved airfoil surface (22A) at perforations (24A). A chemical filtering assembly (26) is located in the port (24) usually engaged with the walls thereof by a retaining ring (26A) which retains a first screen (26B). A sorbent bed (26C) may be sandwiched between first screen (26B) and a second screen (26D), the entire assembly held by the retaining ring against the walls defined in perforations (24A). Molding (29A) press fits into grooves (29B).

When the second airfoil is fastened, as with fasteners (28), to an end plate, as here in end plate (18A), it can been seen that air passing through inlet (I) can be drawn through port (24) by the low pressure created when air flows over curved surface (22A), the air passing from the interior defined by the upper and lower airfoil through the port and through the filtering assembly. Sorbent bed (26C) may be made of Carboxen™, an activated charcoal. Carboxen is available from Scientific Instrument Services, Inc.

Figure 9A:
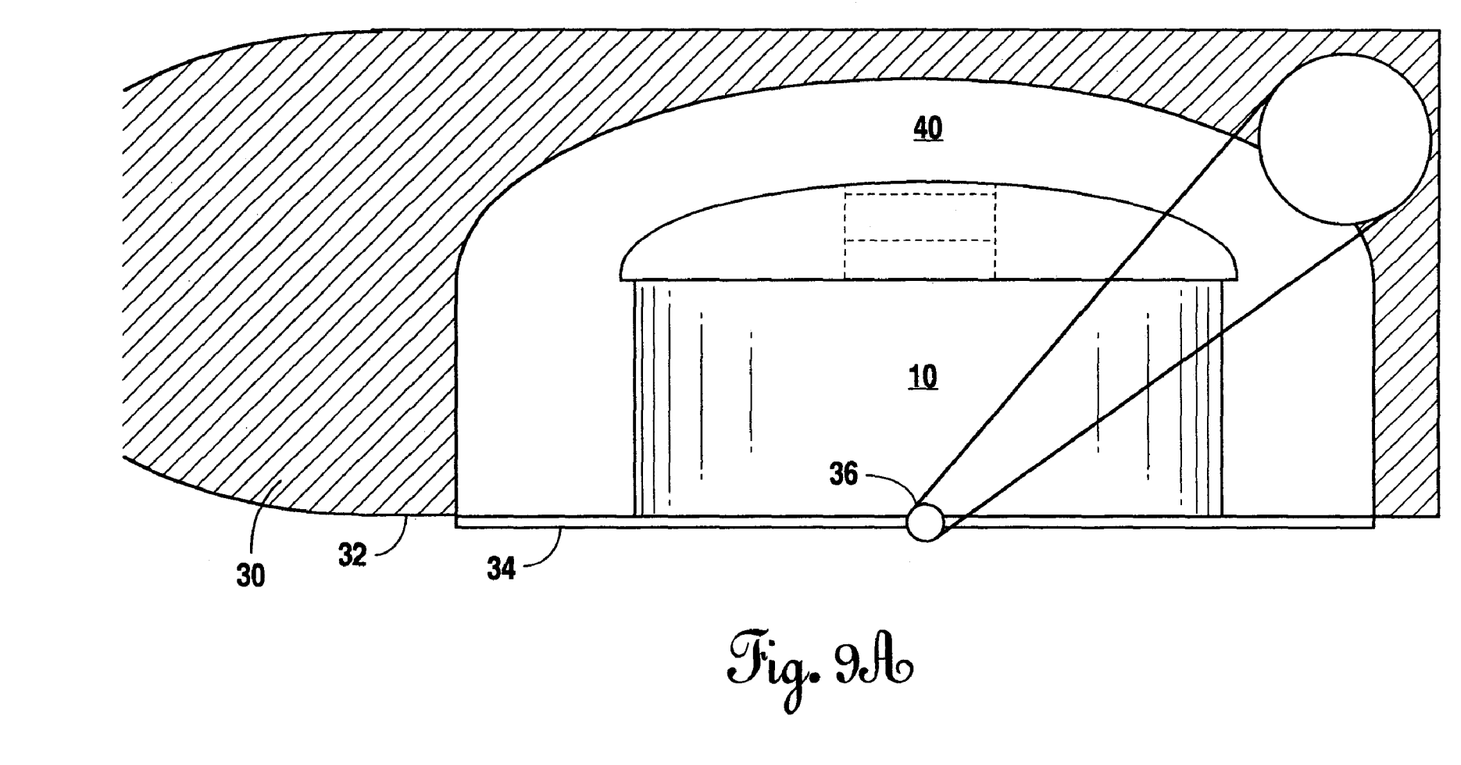
Figure 9B:
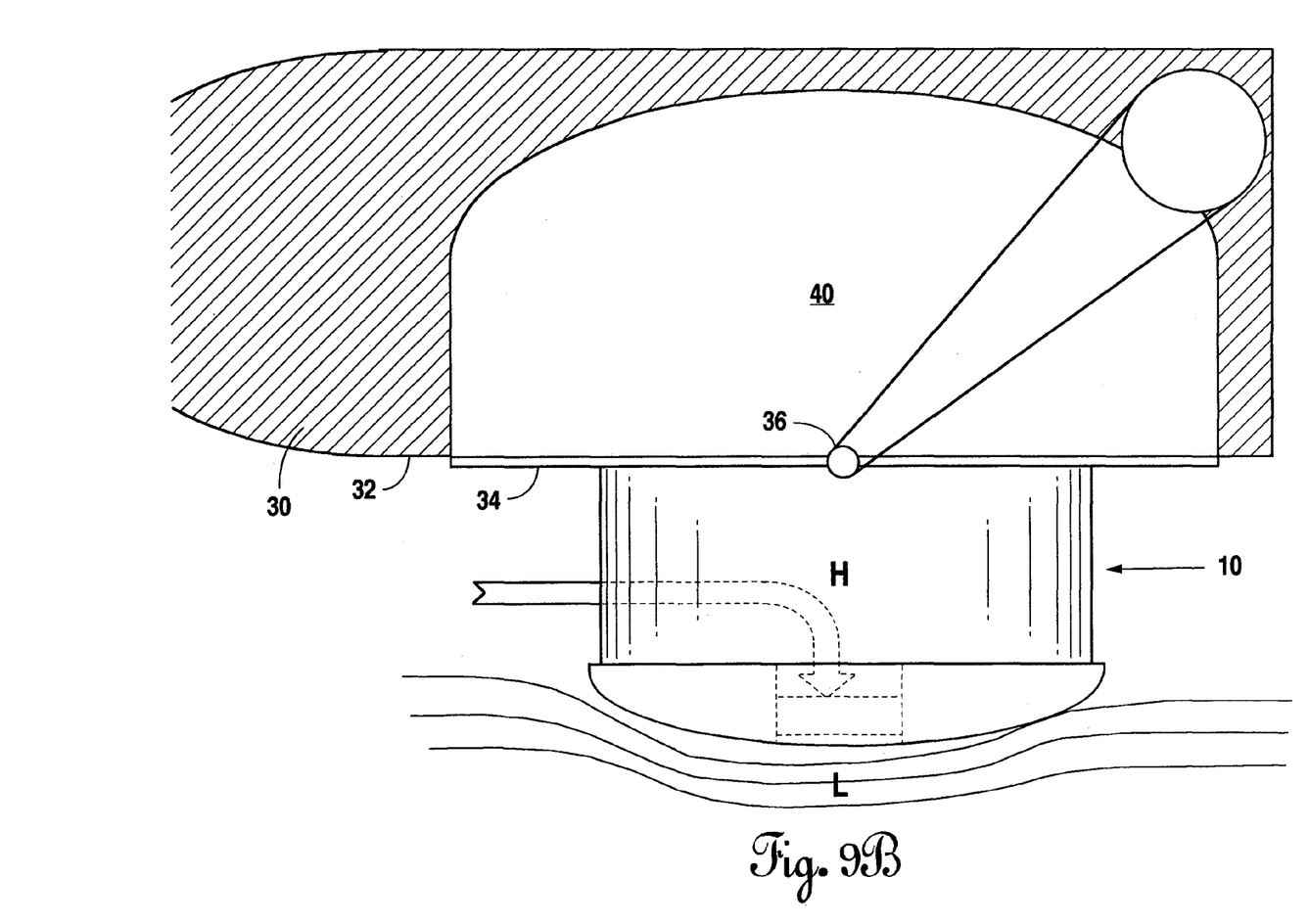

FIGS. 9A and 9B illustrate a method use of an air sampling device (10) as part of a system including an aircraft (30) having fuselage walls (32) and including a plate (34) for engaging the fuselage walls, which plate (34) may be mounted on an axle (36). The axle (36) may be driven by a servo (38). The fuselage may include walls defining a cavity (40) which would be dimensioned to enclose the air sampling device. Activation of the servo may cause the plate to rotate and move the air sampler from a retracted position within the fuselage as illustrated in FIG. 9A to an extended position in the air stream as illustrated in FIG. 9B.

Figure 10:
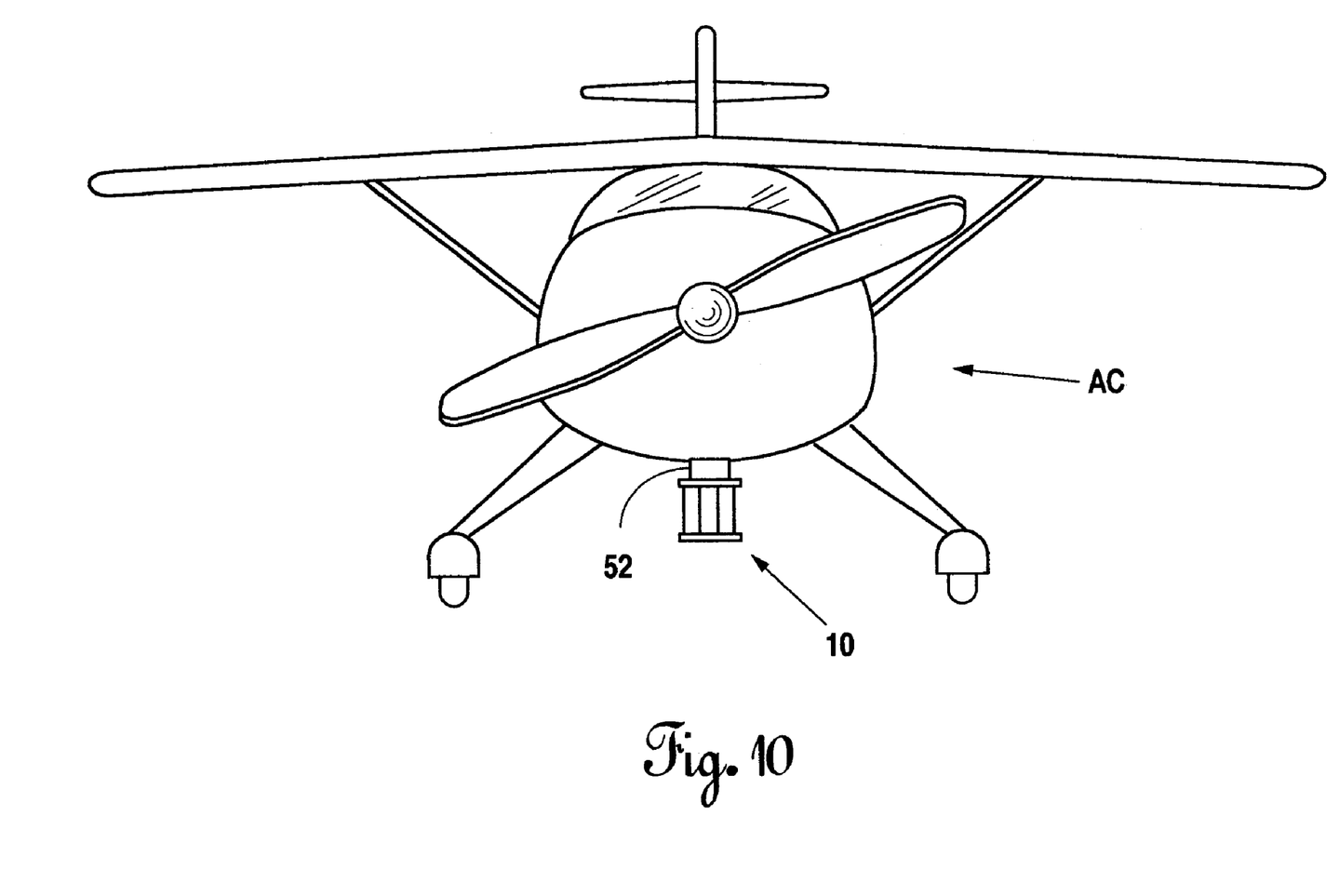

FIG. 10 illustrates an aircraft (AC) here a small, unmanned radio controlled drone including an air sampling system. The air sampling system includes Applicants' air sampling device (10) rigidly mounted to the fuselage on a bracket (52). The bracket positions the air sampling device in the air stream, here below the underside of the fuselage and thus outside the influence of the main wings and the tail of the aircraft.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A device for sampling air, the device comprising:
   an at least partially airfoil shaped frame, the frame including top and bottom opposing surfaces each of the surfaces defining a leading edge and a trailing edge, wherein a part of the frame defines an interior space between the top and bottom opposing surfaces and a part of the frame occupies at least a part of said interior space; and
   a pleated absorbent filter media for engaging the frame, the filter media being capable of absorbing particulate matter from an airstream.

2. The device of claim 1 wherein the absorbent filter media is electrostatically charged.

3. The device of claim 1 wherein the frame defines an opening adjacent the leading edge and adjacent the trailing edge.

4. The device of claim 3 wherein the shape of the opening adjacent its leading edge is optimized such that the average velocity of the air in the opening is substantially equal to the average velocity of the free air stream when there is relative motion of the frame with respect to the air.

5. The device of claim 1 wherein the longest dimension of the frame is between 1.0 and 12.0 inches.

6. The device of claim 1 wherein the total weight of the frame and absorbent material is less than about 5.0 ounces.

7. The device of claim 1 wherein the frame is formed by an injection molding.

8. The device of claim 1 wherein the frame is formed at least partially from one of the following materials: plastic, nylon, carbon fiber, or a composite.

9. The device of claim 1 further including a vehicle to propel the frame through the air and a bracket to mount the frame to the vehicle.

10. A device for sampling air, the device comprising:
   an at least partially airfoil shaped frame, the frame including top and bottom opposing surfaces each of the surfaces defining a leading edge and a trailing edge, wherein a part of the frame defines an interior space between the top and bottom opposing surfaces and a part of the frame occupies at least a part of said interior space, the frame further including at least one end plate for holding the top and bottom opposing surfaces in spaced apart relation; and
   an absorbent filter media for engaging the frame, the filter media being capable of absorbing particulate matter from an airstream.

11. A device for sampling air, the device comprising:
   an at least partially airfoil shaped frame;
   an absorbent filter media for engaging the frame, the filter media being capable of absorbing particulate matter from an airstream; and
   a vehicle being capable of moving through an airstream and being capable of engaging the frame, the frame adapted to include a mounting plate for rotably mounting the frame with respect to the vehicle such that the frame can be moved between a use position in the airstream a stored position out of the airstream.

* * * * *